(12) United States Patent
Spratt et al.

(10) Patent No.: US 9,918,747 B2
(45) Date of Patent: Mar. 20, 2018

(54) BONE ANCHOR ASSEMBLIES AND METHODS WITH IMPROVED LOCKING

(71) Applicant: DePuy Synthes Products, Inc., Raynham, MA (US)

(72) Inventors: Frank Spratt, Boston, MA (US); Philip A. Cormier, Canton, MA (US); Ernest Quintanilha, Norton, MA (US); Sara Dziedzic, North Attleboro, MA (US); Nicholas Pavento, North Attleboro, MA (US); Derek Shaw, North Attleboro, MA (US); Thibault Chandanson, Villers le lac (FR)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/966,531

(22) Filed: Dec. 11, 2015

(65) Prior Publication Data
US 2016/0128733 A1 May 12, 2016

Related U.S. Application Data

(62) Division of application No. 13/826,161, filed on Mar. 14, 2013, now abandoned.

(51) Int. Cl.
*A61B 17/70* (2006.01)
*A61B 90/00* (2016.01)

(52) U.S. Cl.
CPC ...... *A61B 17/7037* (2013.01); *A61B 17/7032* (2013.01); *A61B 17/7035* (2013.01); *A61B 2090/037* (2016.02)

(58) Field of Classification Search
CPC ............ A61B 17/7034; A61B 17/7035; A61B 17/7032; A61B 17/7037; A61B 17/86; A61B 17/8605; A61B 17/8685
See application file for complete search history.

(56) References Cited

U.S. PATENT DOCUMENTS 2,788,045 A   4/1957 Rosan
2,842,180 A   7/1958 Brown et al.
(Continued)

FOREIGN PATENT DOCUMENTS

DE   29903342 U1   6/1999
EP   0470660   2/1992
(Continued)

OTHER PUBLICATIONS

[No Author Listed] Definition of "clip," www.thefreedictionary.com/clip; accessed May 16, 2015.
(Continued)

*Primary Examiner* — Julianna N Harvey
(74) *Attorney, Agent, or Firm* — Nutter McClennen & Fish LLP

(57) ABSTRACT

Various exemplary methods and devices are provided for fixing bone anchors to bone. In general, the methods and devices can allow for a bone anchor to be fixed to a bone at a desired angle to a receiver member. In an exemplary embodiment, a bone anchor assembly is provided that includes a bone anchor configured to engage bone, a receiver member that polyaxially seats a spherical head of the bone anchor, and a compression member seated within the receiver member, proximally of the head of the bone anchor. The compression member can have a distal end with gripping features thereon configured to create at least one line contact and/or one band contact with the head of the bone anchor, thus providing a firm grip on the head of the bone anchor and reducing a risk of slippage of the bone anchor with respect to the receiver member.

18 Claims, 9 Drawing Sheets

(56) References Cited

U.S. PATENT DOCUMENTS

| | | |
|---|---|---|
| 4,124,318 A | 11/1978 | Sagady |
| 4,762,024 A | 8/1988 | Graft |
| 5,009,017 A | 4/1991 | Diekevers et al. |
| 5,129,388 A | 7/1992 | Vignaud et al. |
| 5,154,719 A | 10/1992 | Cotrel |
| 5,306,275 A | 4/1994 | Bryan |
| 5,360,431 A | 11/1994 | Puno et al. |
| 5,385,565 A | 1/1995 | Ray |
| 5,443,467 A | 8/1995 | Biedermann et al. |
| 5,474,555 A | 12/1995 | Puno et al. |
| 5,486,174 A | 1/1996 | Fournet-Fayard et al. |
| 5,487,744 A | 1/1996 | Howland |
| 5,501,684 A | 3/1996 | Schlapfer et al. |
| 5,520,689 A | 5/1996 | Schlapfer et al. |
| 5,562,661 A | 10/1996 | Yoshimi et al. |
| 5,580,246 A | 12/1996 | Fried et al. |
| 5,643,260 A | 7/1997 | Doherty |
| 5,672,176 A | 9/1997 | Biedermann et al. |
| 5,782,833 A | 7/1998 | Haider |
| 5,797,911 A | 8/1998 | Sherman et al. |
| 5,879,350 A | 3/1999 | Sherman et al. |
| 5,885,286 A | 3/1999 | Sherman et al. |
| 5,941,882 A | 8/1999 | Jammet et al. |
| 5,964,591 A | 10/1999 | Beaty et al. |
| 5,989,250 A | 11/1999 | Wagner et al. |
| 6,050,997 A | 4/2000 | Mullane |
| 6,053,917 A | 4/2000 | Sherman et al. |
| 6,056,753 A | 5/2000 | Jackson |
| 6,068,632 A | 5/2000 | Carchidi et al. |
| 6,074,391 A | 6/2000 | Metz-Stavenhagen et al. |
| 6,077,262 A | 6/2000 | Schlapfer et al. |
| 6,090,111 A | 7/2000 | Nichols |
| 6,113,601 A | 9/2000 | Tatar |
| 6,146,383 A | 11/2000 | Studer et al. |
| 6,224,596 B1 | 5/2001 | Jackson |
| 6,224,598 B1 | 5/2001 | Jackson |
| 6,251,112 B1 | 6/2001 | Jackson |
| 6,258,090 B1 | 7/2001 | Jackson |
| 6,261,287 B1 | 7/2001 | Metz-Stavenhagen |
| 6,280,442 B1 | 8/2001 | Barker et al. |
| 6,296,642 B1 | 10/2001 | Morrison et al. |
| 6,302,888 B1 | 10/2001 | Mellinger et al. |
| 6,355,038 B1 | 3/2002 | Pisharodi |
| 6,361,535 B2 | 3/2002 | Jackson |
| 6,379,356 B1 | 4/2002 | Jackson |
| 6,402,757 B1 | 6/2002 | Moore, III et al. |
| 6,440,132 B1 | 8/2002 | Jackson |
| 6,454,768 B1 | 9/2002 | Jackson |
| 6,454,772 B1 | 9/2002 | Jackson |
| 6,458,132 B2 | 10/2002 | Choi et al. |
| 6,475,218 B2 | 11/2002 | Gournay et al. |
| 6,485,491 B1 | 11/2002 | Farris et al. |
| 6,485,494 B1 | 11/2002 | Haider |
| 6,488,681 B2 | 12/2002 | Martin et al. |
| 6,537,276 B2 | 3/2003 | Metz-Stavenhagen |
| 6,540,748 B2 | 4/2003 | Lombardo |
| 6,565,567 B1 | 5/2003 | Haider |
| 6,629,977 B1 | 10/2003 | Wolf |
| 6,660,004 B2 | 12/2003 | Barker et al. |
| 6,663,656 B2 | 12/2003 | Schmieding et al. |
| 6,723,100 B2 | 4/2004 | Biedermann et al. |
| 6,726,480 B1 | 4/2004 | Sutter |
| 6,726,687 B2 | 4/2004 | Jackson |
| 6,730,089 B2 | 5/2004 | Jackson |
| 6,736,820 B2 | 5/2004 | Biedermann et al. |
| 6,740,086 B2 | 5/2004 | Richelsoph |
| 6,755,836 B1 | 6/2004 | Lewis |
| 6,835,196 B2 | 12/2004 | Biedermann et al. |
| 6,843,790 B2 | 1/2005 | Ferree |
| 6,869,433 B2 | 3/2005 | Glascott |
| 6,884,244 B1 | 4/2005 | Jackson |
| 6,974,460 B2 | 12/2005 | Carbone et al. |
| 6,981,973 B2 | 1/2006 | McKinley |
| 6,997,927 B2 | 2/2006 | Jackson |
| 7,018,378 B2 | 3/2006 | Biedermann et al. |
| 7,022,122 B2 | 4/2006 | Amrein et al. |
| 7,083,621 B2 | 8/2006 | Shaolian et al. |
| 7,087,057 B2 | 8/2006 | Konieczynski et al. |
| 7,179,261 B2 | 2/2007 | Sicvol et al. |
| 7,186,255 B2 | 3/2007 | Baynham et al. |
| 7,198,625 B1 | 4/2007 | Hui et al. |
| 7,211,086 B2 | 5/2007 | Biedermann et al. |
| 7,223,268 B2 | 5/2007 | Biedermann |
| 7,235,075 B1 | 6/2007 | Metz-Stavenhagen |
| 7,261,716 B2 | 8/2007 | Strobel et al. |
| 7,264,621 B2 | 9/2007 | Coates et al. |
| 7,291,153 B2 | 11/2007 | Glascott |
| 7,322,981 B2 | 1/2008 | Jackson |
| 7,325,470 B2 | 2/2008 | Kay et al. |
| 7,445,627 B2 | 11/2008 | Hawkes et al. |
| 7,473,267 B2 | 1/2009 | Nguyen et al. |
| 7,559,943 B2 | 7/2009 | Mujwid |
| 7,572,279 B2 | 8/2009 | Jackson |
| 7,591,839 B2 | 9/2009 | Biedermann et al. |
| 7,604,655 B2 | 10/2009 | Warnick |
| 7,615,068 B2 | 11/2009 | Timm et al. |
| 7,625,394 B2 | 12/2009 | Molz, IV et al. |
| 7,670,362 B2 | 3/2010 | Zergiebel |
| 7,674,277 B2 | 3/2010 | Burd et al. |
| 7,678,137 B2 | 3/2010 | Butler et al. |
| 7,678,139 B2 | 3/2010 | Garamszegi et al. |
| 7,682,377 B2 | 3/2010 | Konieczynski et al. |
| 7,686,833 B1 | 3/2010 | Muhanna et al. |
| 7,699,876 B2 | 4/2010 | Barry et al. |
| 7,717,942 B2 | 5/2010 | Schumacher |
| 7,722,649 B2 | 5/2010 | Biedermann et al. |
| 7,727,261 B2 | 6/2010 | Barker et al. |
| 7,731,736 B2 | 6/2010 | Guenther et al. |
| 7,736,380 B2 | 6/2010 | Johnston et al. |
| 7,766,946 B2 | 8/2010 | Bailly |
| 7,785,354 B2 | 8/2010 | Biedermann et al. |
| 7,789,900 B2 | 9/2010 | Levy et al. |
| 7,846,190 B2 | 12/2010 | Ball |
| 7,850,718 B2 | 12/2010 | Bette et al. |
| 7,857,834 B2 | 12/2010 | Boschert |
| 7,867,257 B2 | 1/2011 | Na et al. |
| 7,892,259 B2 | 2/2011 | Biedermann et al. |
| 7,901,413 B1 | 3/2011 | Lewis |
| 7,922,748 B2 | 4/2011 | Hoffman |
| 7,951,173 B2 | 5/2011 | Hammill, Sr. et al. |
| 7,951,175 B2 | 5/2011 | Chao et al. |
| 7,955,363 B2 | 6/2011 | Richelsoph |
| 8,007,522 B2 | 8/2011 | Hutchinson |
| 8,016,862 B2 | 9/2011 | Felix et al. |
| 8,052,724 B2 | 11/2011 | Jackson |
| 8,057,518 B2 | 11/2011 | Frasier et al. |
| 8,066,744 B2 | 11/2011 | Justis et al. |
| 8,066,745 B2 | 11/2011 | Kirschman |
| 8,075,599 B2 | 12/2011 | Johnson et al. |
| 8,083,774 B2 | 12/2011 | Teitelbaum |
| 8,092,494 B2 | 1/2012 | Butler et al. |
| 8,097,023 B2 | 1/2012 | Cline, Jr. et al. |
| 8,097,025 B2 | 1/2012 | Hawkes et al. |
| 8,100,946 B2 | 1/2012 | Strausbaugh et al. |
| 8,114,134 B2 | 2/2012 | Winslow et al. |
| 8,162,989 B2 | 4/2012 | Khalili |
| 8,167,910 B2 | 5/2012 | Nilsson |
| 8,167,912 B2 | 5/2012 | Jacofsky et al. |
| 8,197,517 B1 | 6/2012 | Lab et al. |
| 8,197,518 B2 | 6/2012 | Hammill, Sr. et al. |
| 8,221,471 B2 | 7/2012 | Kovach et al. |
| 8,221,472 B2 | 7/2012 | Peterson et al. |
| 8,236,035 B1 | 8/2012 | Bedor |
| 8,241,341 B2 | 8/2012 | Walker et al. |
| 8,257,396 B2 | 9/2012 | Jackson |
| 8,257,399 B2 | 9/2012 | Biedermann et al. |
| 8,267,968 B2 | 9/2012 | Remington et al. |
| 8,273,112 B2 | 9/2012 | Garamszegi et al. |
| 8,277,490 B2 | 10/2012 | Freeman et al. |
| 8,287,576 B2 | 10/2012 | Barrus |
| 8,298,270 B2 | 10/2012 | Justis et al. |
| 8,298,274 B2 | 10/2012 | Barker, Jr. et al. |
| 8,303,594 B2 | 11/2012 | Lynch et al. |
| 8,308,782 B2 | 11/2012 | Jackson |

(56) References Cited

U.S. PATENT DOCUMENTS

| | | |
|---|---|---|
| 8,313,515 B2 | 11/2012 | Brennan et al. |
| 8,313,516 B2 | 11/2012 | Konieczynski et al. |
| 8,337,530 B2 | 12/2012 | Hestad et al. |
| 8,343,191 B2 | 1/2013 | Matthis et al. |
| 8,377,100 B2 | 2/2013 | Jackson |
| 8,409,260 B2 | 4/2013 | Biedermann et al. |
| 8,430,914 B2 | 4/2013 | Spratt et al. |
| 8,465,528 B2 | 6/2013 | Schumacher |
| 8,465,530 B2 | 6/2013 | Hammill, Sr. et al. |
| 8,491,640 B1 | 7/2013 | Robinson |
| 8,491,641 B2 | 7/2013 | Nihalani |
| 8,556,938 B2 | 10/2013 | Jackson et al. |
| 8,556,941 B2 | 10/2013 | Hutchinson |
| 8,608,746 B2 | 12/2013 | Kolb et al. |
| 8,951,294 B2 | 2/2015 | Gennari et al. |
| 9,155,580 B2 | 10/2015 | Cormier et al. |
| 9,259,247 B2 | 2/2016 | Chandanson et al. |
| 9,402,673 B2 | 8/2016 | Cormier et al. |
| 9,433,445 B2 | 9/2016 | Ramsay et al. |
| 2002/0133159 A1 | 9/2002 | Jackson |
| 2003/0023243 A1 | 1/2003 | Biedermann et al. |
| 2003/0055426 A1 | 3/2003 | Carbone et al. |
| 2003/0073996 A1 | 4/2003 | Doubler et al. |
| 2003/0100896 A1 | 5/2003 | Biedermann et al. |
| 2003/0125741 A1 | 7/2003 | Biedermann et al. |
| 2003/0153911 A1 | 8/2003 | Shluzas |
| 2004/0049190 A1 | 3/2004 | Biedermann et al. |
| 2004/0116929 A1 | 6/2004 | Barker et al. |
| 2004/0153077 A1 | 8/2004 | Biedermann et al. |
| 2004/0162560 A1 | 8/2004 | Raynor et al. |
| 2004/0186473 A1 | 9/2004 | Cournoyer et al. |
| 2004/0186478 A1 | 9/2004 | Jackson |
| 2004/0193160 A1 | 9/2004 | Richelsoph |
| 2004/0243126 A1 | 12/2004 | Carbone et al. |
| 2005/0055026 A1 | 3/2005 | Biedermann et al. |
| 2005/0080415 A1 | 4/2005 | Keyer et al. |
| 2005/0153077 A1 | 7/2005 | Gedeon et al. |
| 2005/0154391 A1 | 7/2005 | Doherty et al. |
| 2005/0154393 A1 | 7/2005 | Doherty et al. |
| 2005/0159750 A1 | 7/2005 | Doherty |
| 2005/0182401 A1 | 8/2005 | Timm et al. |
| 2005/0187548 A1 | 8/2005 | Butler et al. |
| 2005/0216003 A1 | 9/2005 | Biedermann et al. |
| 2005/0228326 A1 | 10/2005 | Kalfas et al. |
| 2005/0273101 A1 | 12/2005 | Schumacher |
| 2005/0277928 A1* | 12/2005 | Boschert ............ A61B 17/7037 606/328 |
| 2006/0025771 A1 | 2/2006 | Jackson |
| 2006/0083603 A1 | 4/2006 | Jackson |
| 2006/0084995 A1 | 4/2006 | Biedermann et al. |
| 2006/0100621 A1 | 5/2006 | Jackson |
| 2006/0100622 A1 | 5/2006 | Jackson |
| 2006/0106383 A1 | 5/2006 | Biedermann et al. |
| 2006/0149241 A1 | 7/2006 | Richelsoph et al. |
| 2006/0161153 A1 | 7/2006 | Hawkes et al. |
| 2006/0200128 A1 | 9/2006 | Mueller |
| 2006/0241599 A1 | 10/2006 | Konieczynski et al. |
| 2006/0264933 A1 | 11/2006 | Baker et al. |
| 2007/0055244 A1 | 3/2007 | Jackson |
| 2007/0118117 A1 | 5/2007 | Altarac et al. |
| 2007/0118123 A1 | 5/2007 | Strausbaugh et al. |
| 2007/0123862 A1 | 5/2007 | Warnick |
| 2007/0123870 A1 | 5/2007 | Jeon |
| 2007/0260246 A1 | 11/2007 | Biedermann |
| 2007/0265621 A1 | 11/2007 | Matthis et al. |
| 2007/0270813 A1 | 11/2007 | Garamszegi |
| 2007/0293862 A1 | 12/2007 | Jackson |
| 2008/0021473 A1 | 1/2008 | Butler et al. |
| 2008/0045953 A1 | 2/2008 | Garamszegi |
| 2008/0119852 A1 | 5/2008 | Dalton et al. |
| 2008/0132957 A1 | 6/2008 | Matthis et al. |
| 2008/0147129 A1 | 6/2008 | Biedermann et al. |
| 2008/0161859 A1 | 7/2008 | Nilsson |
| 2008/0200956 A1 | 8/2008 | Beckwith et al. |
| 2008/0215100 A1 | 9/2008 | Matthis et al. |
| 2008/0269805 A1 | 10/2008 | Dekutoski et al. |
| 2008/0269809 A1 | 10/2008 | Garamszegi |
| 2008/0288001 A1 | 11/2008 | Cawley et al. |
| 2008/0294202 A1 | 11/2008 | Peterson et al. |
| 2008/0312692 A1 | 12/2008 | Brennan et al. |
| 2009/0005813 A1 | 1/2009 | Crall et al. |
| 2009/0012567 A1 | 1/2009 | Biedermann et al. |
| 2009/0018591 A1 | 1/2009 | Hawkes et al. |
| 2009/0118772 A1 | 5/2009 | Diederich et al. |
| 2009/0163962 A1 | 6/2009 | Dauster et al. |
| 2009/0182384 A1 | 7/2009 | Wilcox et al. |
| 2009/0198280 A1 | 8/2009 | Spratt et al. |
| 2009/0216280 A1 | 8/2009 | Hutchinson |
| 2009/0228051 A1 | 9/2009 | Kolb et al. |
| 2009/0228053 A1 | 9/2009 | Kolb et al. |
| 2009/0254125 A1 | 10/2009 | Predick |
| 2009/0264933 A1 | 10/2009 | Carls et al. |
| 2009/0287261 A1 | 11/2009 | Jackson |
| 2009/0326587 A1 | 12/2009 | Matthis et al. |
| 2010/0004693 A1 | 1/2010 | Miller et al. |
| 2010/0010547 A1 | 1/2010 | Beaurain et al. |
| 2010/0020272 A1 | 1/2010 | Kim et al. |
| 2010/0023061 A1 | 1/2010 | Randol et al. |
| 2010/0030272 A1 | 2/2010 | Winslow et al. |
| 2010/0103099 A1 | 4/2010 | Lee |
| 2010/0114174 A1 | 5/2010 | Jones et al. |
| 2010/0152785 A1 | 6/2010 | Forton et al. |
| 2010/0160977 A1 | 6/2010 | Gephart et al. |
| 2010/0168747 A1 | 7/2010 | Lynch et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0222827 A1 | 9/2010 | Griffiths et al. |
| 2010/0234891 A1 | 9/2010 | Freeman et al. |
| 2010/0305621 A1 | 12/2010 | Wang et al. |
| 2010/0312279 A1 | 12/2010 | Gephart et al. |
| 2011/0046683 A1 | 2/2011 | Biedermann et al. |
| 2011/0106179 A1 | 5/2011 | Prevost et al. |
| 2011/0160778 A1 | 6/2011 | Elsbury |
| 2011/0160779 A1 | 6/2011 | Schlaepfer et al. |
| 2011/0190822 A1 | 8/2011 | Spitler et al. |
| 2011/0213424 A1 | 9/2011 | Biedermann et al. |
| 2011/0245876 A1 | 10/2011 | Brumfield |
| 2011/0245877 A1 | 10/2011 | Pisharodi |
| 2011/0251650 A1 | 10/2011 | Biedermann et al. |
| 2011/0270322 A1 | 11/2011 | Olsen et al. |
| 2011/0276098 A1 | 11/2011 | Biedermann et al. |
| 2011/0282399 A1 | 11/2011 | Jackson |
| 2011/0288592 A1 | 11/2011 | McKinley |
| 2011/0288599 A1 | 11/2011 | Michielli et al. |
| 2011/0295321 A1 | 12/2011 | Hutchinson |
| 2012/0010661 A1 | 1/2012 | Farris et al. |
| 2012/0022593 A1 | 1/2012 | Kovach et al. |
| 2012/0035670 A1 | 2/2012 | Jackson et al. |
| 2012/0046701 A1 | 2/2012 | Gennari et al. |
| 2012/0059425 A1 | 3/2012 | Biedermann |
| 2012/0059426 A1 | 3/2012 | Jackson et al. |
| 2012/0078307 A1 | 3/2012 | Nihalani |
| 2012/0083845 A1 | 4/2012 | Winslow et al. |
| 2012/0089194 A1 | 4/2012 | Strausbaugh et al. |
| 2012/0136395 A1* | 5/2012 | Biedermann ...... A61B 17/7037 606/279 |
| 2012/0143266 A1* | 6/2012 | Jackson ............ A61B 17/7008 606/328 |
| 2012/0150239 A1 | 6/2012 | Garamszegi |
| 2012/0165882 A1 | 6/2012 | Biedermann et al. |
| 2012/0179209 A1 | 7/2012 | Biedermann et al. |
| 2012/0185003 A1 | 7/2012 | Biedermann et al. |
| 2012/0197313 A1 | 8/2012 | Cowan |
| 2012/0209336 A1 | 8/2012 | Jackson et al. |
| 2012/0253404 A1 | 10/2012 | Timm et al. |
| 2012/0277805 A1 | 11/2012 | Farris |
| 2012/0303070 A1 | 11/2012 | Jackson |
| 2012/0310290 A1 | 12/2012 | Jackson |
| 2012/0316605 A1 | 12/2012 | Palagi |
| 2012/0328394 A1 | 12/2012 | Biedermann et al. |
| 2012/0330364 A1 | 12/2012 | Jacofsky et al. |
| 2013/0013003 A1 | 1/2013 | Carbone et al. |

(56) References Cited

U.S. PATENT DOCUMENTS

| | | |
|---|---|---|
| 2013/0046350 A1* | 2/2013 | Jackson ............ A61B 17/7005 606/305 |
| 2013/0053901 A1 | 2/2013 | Cormier et al. |
| 2013/0096618 A1 | 4/2013 | Chandanson et al. |
| 2013/0096623 A1 | 4/2013 | Biedermann et al. |
| 2013/0103093 A1 | 4/2013 | Biedermann et al. |
| 2013/0110172 A1 | 5/2013 | Biedermann et al. |
| 2013/0110180 A1 | 5/2013 | Doubler et al. |
| 2013/0211467 A1 | 8/2013 | Dickinson |
| 2014/0018861 A1 | 1/2014 | Hutchinson |
| 2014/0025119 A1 | 1/2014 | Biedermann et al. |
| 2014/0094849 A1 | 4/2014 | Spratt et al. |
| 2014/0142633 A1 | 5/2014 | Jackson et al. |
| 2014/0277153 A1 | 9/2014 | Spratt et al. |
| 2014/0277157 A1 | 9/2014 | Chandanson et al. |
| 2014/0277158 A1 | 9/2014 | Spratt et al. |
| 2014/0277159 A1 | 9/2014 | Spratt et al. |
| 2014/0277161 A1 | 9/2014 | Spratt et al. |
| 2014/0277162 A1 | 9/2014 | Kostuik et al. |
| 2014/0277189 A1 | 9/2014 | Spratt et al. |
| 2016/0135848 A1 | 5/2016 | Chandanson et al. |

FOREIGN PATENT DOCUMENTS

| | | | |
|---|---|---|---|
| EP | 857465 | A1 | 8/1998 |
| EP | 1 295 566 | A1 | 3/2003 |
| EP | 1 570 794 | A1 | 9/2005 |
| EP | 1 694 229 | A1 | 8/2006 |
| EP | 1 774 919 | A1 | 4/2007 |
| EP | 1 795 134 | A1 | 6/2007 |
| EP | 2 070 485 | A1 | 6/2009 |
| EP | 2 129 310 | A1 | 12/2009 |
| EP | 2 272 451 | A1 | 1/2011 |
| EP | 2 286 748 | A1 | 2/2011 |
| EP | 2 455 028 | A1 | 5/2012 |
| WO | 91/016020 | A1 | 10/1991 |
| WO | 2004/058081 | A1 | 7/2004 |
| WO | 2008/024937 | A2 | 2/2008 |
| WO | 2008/119006 | A1 | 10/2008 |
| WO | 2009/073655 | A1 | 6/2009 |
| WO | WO 2009073655 A1 * | 6/2009 | ......... A61B 17/7037 |
| WO | 2010/056846 | A2 | 5/2010 |
| WO | 2011/059732 | A1 | 5/2011 |
| WO | 2011/109009 | A1 | 9/2011 |
| WO | 2011/127065 | A1 | 10/2011 |
| WO | 2012/024665 | A2 | 2/2012 |
| WO | 2012/030712 | A1 | 3/2012 |
| WO | 2012/035479 | A2 | 3/2012 |
| WO | 2012/060868 | A1 | 5/2012 |
| WO | 2013/028851 | A1 | 2/2013 |

OTHER PUBLICATIONS

[No Author Listed] Expedium Dual Innie Brochure, DePuy Spine, Aug. 1, 2004.
[No Author Listed] Moss Miami Polyaxial Reduction Screw Surgical Technique, DePuy AcroMed, Inc. 1998.
[No Author Listed] Viper 2 MIS Extended Tab, DePuy Spine, Inc., Feb. 1, 2009.
Duerig, "Engineering Aspects of Shape Memory Alloys", T W Duerig et al, on p. 370, Butterworth-Heinemann (1990).
[No Author Listed] A New Angle on Correction. Expedium. DePuy. 2009. 2 pages.
[No Author Listed] Straight Talk with Expedium. Expedium. 10 pages. Jul. 2007.
[No Author Listed] Surgical Technique Guide and Ordering Information. Expedium. DePuy Spine Inc. Sep. 2011. 24 Pages.
[No Author Listed] Value Analysis Brief—Expedium Favored Angle Screw. DePuy Synthes Spine. Aug. 2012. 4 pages.
[No Author Listed] Viper 2 MIS Spine System. System Guide. DePuy Spine Inc. Sep. 2011. 60 pages.
International Search Report for PCT/US14/021198 dated Jun. 5, 2014 (3 Pages).
U.S. Appl. No. 61/706,860, filed Sep. 28, 2012 (66 pages).
International Search Report and Written Opinion for Application No. PCT/US2013/060350, dated Jan. 3, 2014 (9 pages).
International Preliminary Report on Patentability for Application No. PCT/US2014/021198, dated Sep. 24, 2015 (7 pages).

* cited by examiner

BONE ANCHOR ASSEMBLIES AND METHODS WITH IMPROVED LOCKING

CROSS-REFERENCE TO RELATED APPLICATIONS

This application is a divisional of U.S. patent application Ser. No. 13/826,161 filed on Mar. 14, 2013, entitled "BONE ANCHOR ASSEMBLIES AND METHODS WITH IMPROVED LOCKING," which is hereby incorporated by reference in its entirety.

FIELD

The present invention relates to methods and devices for correcting a spine, and in particular to bone anchor assemblies and methods of using the same.

BACKGROUND

Bone anchors may be used in orthopedic surgery to fix bone during healing or during a fusion process. In spinal surgery, bone anchors may be used with spinal fixation elements, such as spinal rods, to stabilize multiple vertebrae either rigidly, in which no relative motion between the vertebrae is desired, or dynamically, in which limited, controlled motion between the vertebrae is desired. Fixation elements can help to support the spine in a desired alignment, for example by defining a shape towards which a deformed spine is to be corrected. Attaching the vertebrae to the fixation element causes vertebrae which are out of position to be drawn towards the fixation element, so that they can then be retained in a correct alignment against forces imposed by soft tissue tending to revert the configuration of the spine towards the deformed shape. Correction of the spinal deformation can involve application to the vertebrae of translational forces, torsional forces, or combinations thereof to cause vertebrae to translate and/or rotate.

Surgical procedures using bone anchors often require that the bone anchor be secured to the bone at a predetermined angle to a surface of the bone. Traditional bone anchors can include a shaft having a spherical head that is polyaxially seated in a rod-receiving member and that can be secured at a fixed angle to the rod-receiving member by a compression member disposed proximally of the head. Traditional compression members have distal surfaces that are formed as a negative of the head and exert a distal force on the head to maintain the shaft at the predetermined angle. However, where the shaft is positioned at an angle to a longitudinal axis of the compression member, a contact surface area between the compression member and the head can be reduced, which can increase a risk of slippage between the bone anchor and the compression member. Slippage between the bone anchor and the compression member can cause the bone anchor to move from a desired angle and can therefore compromise the effectiveness of the bone anchor for correcting spinal deformities.

Accordingly, there remains a need for improved methods and devices for bone anchor fixation.

SUMMARY

The present invention generally provides methods and devices for fixing a bone anchor to a bone. In one aspect, a bone anchor assembly is provided that can include a bone anchor having a proximal head portion and a distal shank portion, a receiver member having a polyaxial seat formed therein and configured to polyaxially seat the head portion of the bone anchor, and a compression member configured to be disposed within the receiver member and having a distal end configured such that, when the compression member is locked relative to the receiver member, the distal end grips the head portion of the bone anchor with greater friction as compared with a distal end formed as a negative of the head portion of the bone anchor.

The compression member can have a variety of configurations. In one embodiment, the distal end of the compression member can include a sidewall having an inner cylindrical surface, an outer surface, and a planar distal-facing surface extending between the inner and outer surfaces. In another embodiment, the distal end of the compression member can include a sidewall having an inner cylindrical surface, an outer surface, and a conical distal-facing surface extending between the inner and outer surfaces. In yet another embodiment, the distal end of the compression member can include a sidewall having an inner spherical surface with a series of grooves that define a plurality of ring-shaped teeth extending inwards from the inner spherical surface. Each of the plurality of teeth can include a sharp crest configured to contact the head portion of the bone anchor along a ring-shaped line, and/or each of plurality of teeth can include a crest defined by a spherical surface configured to contact the head portion of the bone anchor along a ring-shaped band. In another embodiment, each of the plurality of teeth can include a crest defined by a conical surface configured to deform into contact with the head portion of the bone anchor along a ring-shaped band.

The compression member can also have various configurations, and in one embodiment can include a sidewall that has a first hemicylindrical portion comprising an inner spherical surface and a second hemicylindrical portion comprising an inner cylindrical surface, an outer surface, and a conical distal-facing surface extending between the inner and outer surfaces. The compression member can thus provide uneven contact with the head portion of the bone anchor, thereby compressing the head portion of the bone anchor between the first hemicylindrical portion and the second hemicylindrical portion. In another embodiment, the compression member can include a first inner spherical surface having a first radius and a second inner spherical surface extending distally from the first inner spherical surface, the second inner spherical sidewall having a second radius that is greater than the first radius. At least one of the first radius and the second radius can be less than a radius of the head portion of the bone anchor such that the compression member forms an interference fit with the head portion of the bone anchor.

In another aspect, a bone anchor assembly is provided that includes a bone anchor having a proximal head portion and a distal shank portion, a receiver member having a polyaxial seat formed in a distal end thereof and configured to polyaxially seat the head portion of the bone anchor, and a compression member configured to be disposed within the receiver member. The compression member can have a polyaxial seat formed in a distal end thereof and configured to polyaxially seat the head portion of the bone anchor. The compression member can also have a surface feature formed in the polyaxial seat that is configured to make at least one of line contact and band contact with the head portion of the bone anchor to substantially prevent movement of the head portion of the bone anchor relative to the receiver member when the compression member is locked relative to the receiver member. The bone anchor assembly can have a variety of configurations, including those previously discussed. For example, the surface feature can be in the form of at least one ring-shaped tooth having a crest configured to make ring-shaped line contact with the head portion of the bone anchor. In another embodiment, the compression member can include a sidewall having a first hemicylindrical portion comprising an inner spherical surface and a second hemicylindrical portion comprising an inner cylindrical surface. The sidewall can also include an outer surface and a conical distal-facing surface extending between the inner and outer surfaces. In other embodiments, the polyaxial seat of the receiver member can include at least one ring-shaped tooth having a crest configured to make ring-shaped line contact with the head portion of the bone anchor.

In another aspect, a method is provided that includes the steps of advancing a bone anchor having a proximal head portion and a distal shank portion into a bone, the head portion of the bone anchor being seated in a polyaxial seat formed in a receiver member, and advancing a compression member disposed within the receiver member such that the compression member grips the head portion of the bone anchor with greater friction as compared with a compression member formed as a negative of the head portion of the bone anchor. Advancing the compression member can comprise forcing a distal end of the compression member defined by an inner cylindrical surface, an outer surface, and a planar distal-facing surface extending between the inner and outer surfaces, into contact with the head portion of the bone anchor. The method can also include, after advancing the bone anchor and before advancing the compression member, positioning a spinal fixation rod within the receiver member and proximal of the compression member. In one embodiment, advancing the compression member can comprise applying a closure mechanism to the receiver member to apply a distally directed force to the spinal fixation element and the compression member to thereby lock the spinal fixation element and the bone anchor in a fixed position relative to the receiver member.

The present invention further provides devices, systems, and methods as claimed.

BRIEF DESCRIPTION OF THE DRAWINGS

The invention will be more fully understood from the following detailed description taken in conjunction with the accompanying drawings, in which.

DETAILED DESCRIPTION

Figure 1A:
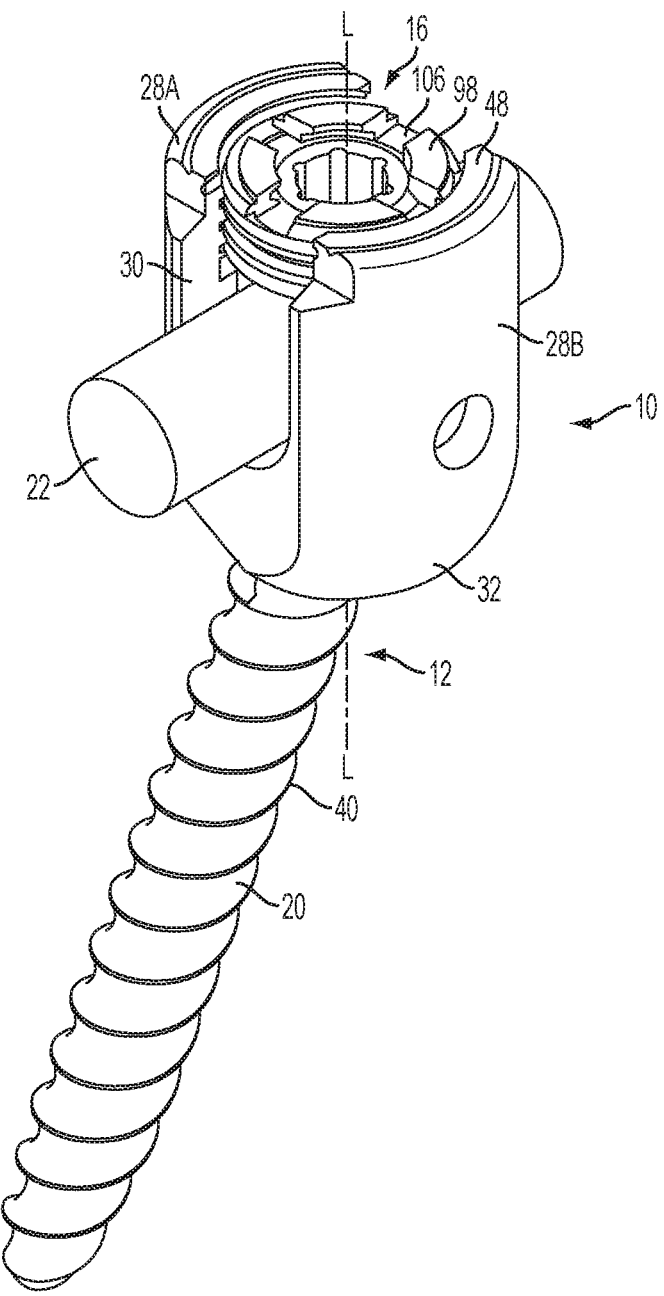
FIG. 1A is a perspective view of a prior art bone anchor assembly.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for fixing bone anchors to bone. In general, the methods and devices can allow for a bone anchor to be fixed to a bone at a desired angle relative to a receiver member. In an exemplary embodiment, a bone anchor assembly is provided that includes a bone anchor configured to engage bone, a receiver member that polyaxially seats a spherical head of the bone anchor, and a compression member for securing the receiver member at a fixed angle with respect to the bone anchor. The compression member can be seated within the receiver member, proximally of the head of the bone anchor, and can have a distal end with one or more gripping features thereon configured to grip the head of the bone anchor, even where the bone anchor is oriented at an angle to a longitudinal axis of the compression member. By way of non-limiting example, the one or more gripping features can be configured to create at least one of a line contact and/or a band contact with the head of the bone anchor, thus providing a firm grip on the head of the bone anchor and reducing a risk of slippage of the bone anchor with respect to the receiver member.

FIGS. 1A-1D illustrate a prior art bone anchor assembly 10 including a bone anchor 12, a receiver member 14 for receiving a spinal fixation element, such as a spinal rod 22, to be coupled to the bone anchor 12, and a closure mechanism 16 to capture a spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end 26 having a pair of spaced apart arms 28A, 28B defining a recess 30 therebetween and a distal end 32 having an inner surface 35 for polyaxially seating the proximal head 18 of the bone anchor 12 and distal end surface 34 defining an opening through which at least a portion of the bone anchor 12 extends. The closure mechanism 16 can be positionable between and can engage the arms 28A, 28B to capture a spinal fixation element, e.g., a spinal rod 22, within the receiver member 14 and fix the spinal fixation element with respect to the receiver member 14.

The proximal head 18 of the bone anchor 12 is generally in the shape of a truncated sphere having a planar proximal surface 36 and an approximately spherically-shaped distal surface 38. The illustrated bone anchor assembly is a polyaxial bone anchor designed for posterior implantation in the pedicle or lateral mass of a vertebra. The proximal head 18 of the bone anchor 12 engages the distal end 32 of the receiver member 14 in a ball and socket like arrangement in which the proximal head 18 the distal shaft 20 can pivot relative to the receiver member 14. The distal surface 38 of the proximal head 18 of the bone anchor 12 and a mating surface within the distal end 32 of the receiver member 14 can have any shape that facilitates this arrangement, including, for example, spherical (as illustrated), toroidal, conical, frustoconical, and any combinations of these shapes.

The distal shaft 20 of the bone anchor 12 can be configured to engage bone and, in the illustrated embodiment, includes an external bone engaging thread 40. The thread form for the distal shaft 20, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Provisional Patent Application Ser. No. 61/527,389, filed Aug. 25, 2011, both of which are incorporated herein by reference. The distal shaft 20 can also include other structures for engaging bone, including a hook. The distal shaft 20 of the bone anchor 12 can be cannulated, having a central passage or cannula extending the length of the bone anchor to facilitate delivery of the bone anchor over a guide wire in, for example, minimally-invasive procedures. Other components of the bone anchor assembly, including, for example, the closure member 16, the receiver member 14, and the compression member 60 (discussed below) can be cannulated or otherwise have an opening to permit delivery over a guide wire or to permit the insertion of a driver instrument to manipulate the bone anchor. The distal shaft 20 can also include one or more sidewall openings or fenestrations that communicate with the cannula to permit bone in-growth or to permit the dispensing of bone cement or other materials through the bone anchor 12. The sidewall openings can extend radially from the cannula through the sidewall of the distal shaft 20. Exemplary systems for delivering bone cement to the bone anchor assembly 10 and alternative bone anchor configurations for facilitating cement delivery are described in U.S. Patent Application Publication No. 2010/0114174, filed on Oct. 29, 2009, which is hereby incorporated herein by reference. The distal shaft 20 of the bone anchor 12 can also be coated with materials to permit bone growth, such as, for example, hydroxyl apatite, and the bone anchor assembly 10 can be coated partially or entirely with anti-infective materials, such as, for example, tryclosan.

The proximal end 26 of the receiver member 14 includes a pair of spaced apart arms 28A, 28B defining a U-shaped recess 30 therebetween for receiving a spinal fixation element, e.g., a spinal rod 22. Each of the arms 28A, 28B can extend from the distal end 32 of the receiver member 14 to a free end. The outer surfaces of each of the arms 28A, 28B can include a feature, such as a recess, dimple, notch, projection, or the like, to facilitate connection of the receiver member 14 to instruments. For example, the outer surface of each arm 28A, 28B can include an arcuate groove at the respective free end of the arms. Such grooves are described in more detail in U.S. Pat. No. 7,179,261, issued on Feb. 20, 2007, which is hereby incorporated herein by reference. At least a portion of the proximal end surface 48 of the receiver member 12 defines a plane Y. The receiver member 14 has a central longitudinal axis L.

The distal end 32 of the receiver member 14 includes a distal end surface 34 which is generally annular in shape defining a circular opening through which at least a portion of the bone anchor 12 extends. For example, the distal shaft 20 of the bone anchor 12 can extend through the opening. At least a portion of the distal end surface 34 defines a plane X.

The bone anchor 12 can be selectively fixed relative to the receiver member 14. Prior to fixation, the bone anchor 12 is movable relative to the receiver member 14 within a cone of angulation generally defined by the geometry of the distal end 32 of the receiver member and the proximal head 18 of the bone anchor 12. The illustrated bone anchor is a favored-angle polyaxial screw in which the cone of angulation is biased in one direction. In this manner, the bone anchor 12 is movable relative to the receiver member 14 in at least a first direction, indicated by arrow A in FIG. 1D, at a first angle C relative to the central longitudinal axis L of the receiver member 14. The bone anchor 12 is also movable in at least a second direction, indicated by arrow B in FIG. 1D, at a second angle D relative to the longitudinal axis L. The first angle C is greater than the second angle D and, thus, the shaft 20 of the bone anchor 12 is movable more in the direction indicated by arrow A than in the direction indicated by arrow B. The distal shaft 20 of the bone anchor 12 defines a neutral axis 48 with respect to the receiver member 14. The neutral axis 48 can be perpendicular to the plane X defined by the distal end surface 34 and intersects the center point of the opening in the distal end surface 34 through which the distal shaft 20 of the bone anchor 12 extends. The neutral axis 48 can be oriented at an angle to the central longitudinal axis L of the receiver member 14. The plane Y defined by at least a portion of the proximal end surface 48 of the receiver member 14 intersects the plane X defined by at least a portion of the distal end surface 34 of the receiver member 12. The proximal end 26 of the receiver member 14 can include a proximal first bore 50 coaxial with a first central longitudinal axis N (which is coincident with longitudinal axis L) and a distal second bore 52 coaxial with a second central longitudinal axis M (which is coincident with the neutral axis 48) and the first central longitudinal axis N and second central longitudinal axis M can intersect one another. The angle between the plane X and the plane Y and the angle between the axis L and the axis M can be selected to provide the desired degree of biased angulation. Examples of favored angled polyaxial screws are described in more detail in U.S. Pat. No. 6,974,460, issued on Dec. 13, 2005, and in U.S. Pat. No. 6,736,820, issued on May 18, 2004, both of which are hereby incorporated herein by reference. Alternatively, the bone anchor assembly can be a conventional (non-biased) polyaxial screw in which the bone anchor pivots in the same amount in every direction and has a neutral axis that is coincident with the central longitudinal axis L of the receiver member.

The spinal fixation element, e.g., the spinal rod 22, can either directly contact the proximal head 18 of the bone anchor 12 or can contact an intermediate element, e.g., a compression member 60. The compression member 60 can be positioned within the receiver member 14 and interposed between the spinal rod 22 and the proximal head 18 of the bone anchor 12 to compress the distal outer surface 38 of the proximal head 18 into direct, fixed engagement with the distal inner surface of the receiver member 14. A proximal portion of the compression member 60 can include a pair of spaced apart arms 62A and 62B defining a U-shaped seat 64 for receiving the spinal rod 22. A distal portion of the compression member 60 can include a sidewall having an inner cylindrical surface 67 that is connected to an outer cylindrical surface 68 by a distal-facing surface 66.

At least a portion of the distal surface 66 of the compression member 60 can be shaped as a negative of the proximal portion 18 of the bone anchor 20, against which the distal surface 66 abuts when the compression member 60 is fully inserted into the receiver member 14. Thus, when the shaft 20 of the bone anchor 12 is oriented along the longitudinal axis L, the contact area between the distal surface 66 of the compression member 60 and the proximal head 18 is maximized. Where the angle of the shaft 20 with respect to the longitudinal axis L is not zero, however, the contact area between the distal surface 66 of the compression member 60 and the head 18 can be reduced, thus increasing a risk of slippage of the bone anchor 12 with respect to the receiver member 14.

Figure 1B:
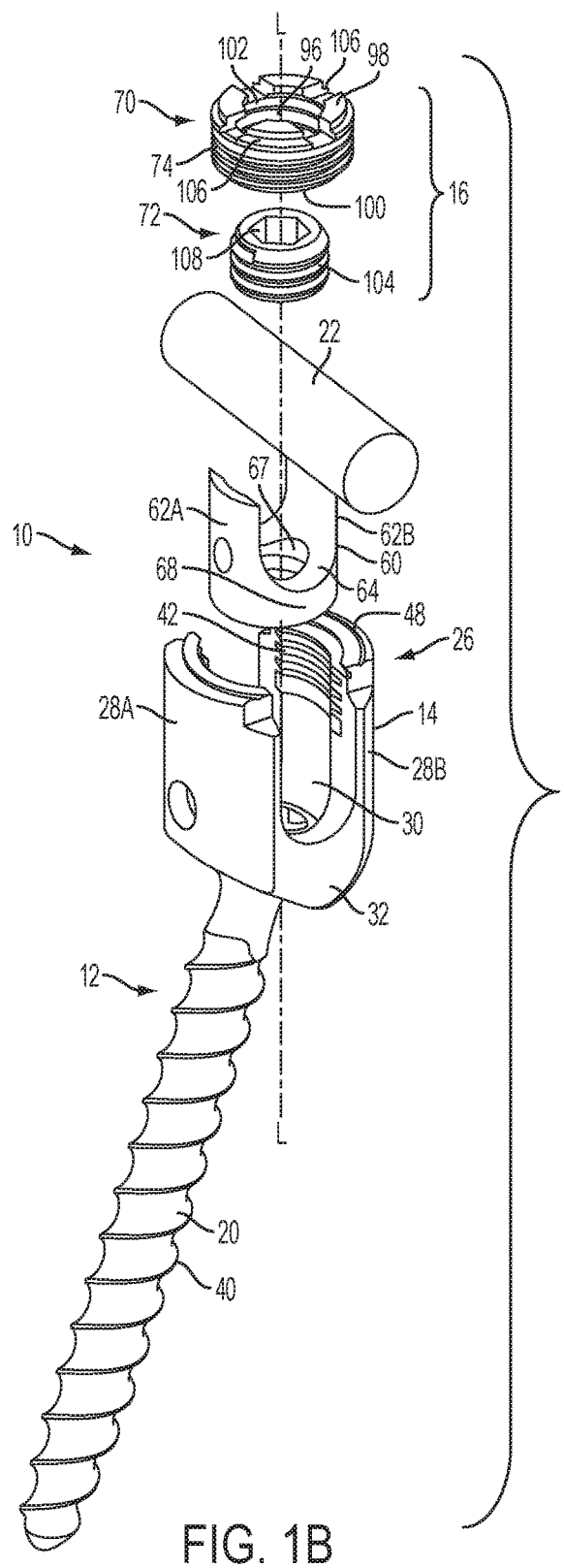
FIG. 1B is an exploded view of the bone anchor assembly of FIG. 1A.
Figure 1C:
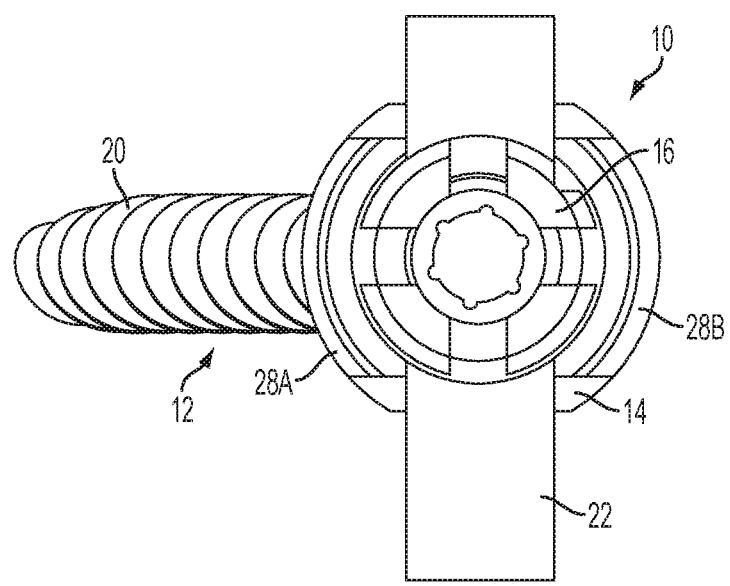
FIG. 1C is a top view of the bone anchor assembly of FIG. 1A.
Figure 1D:
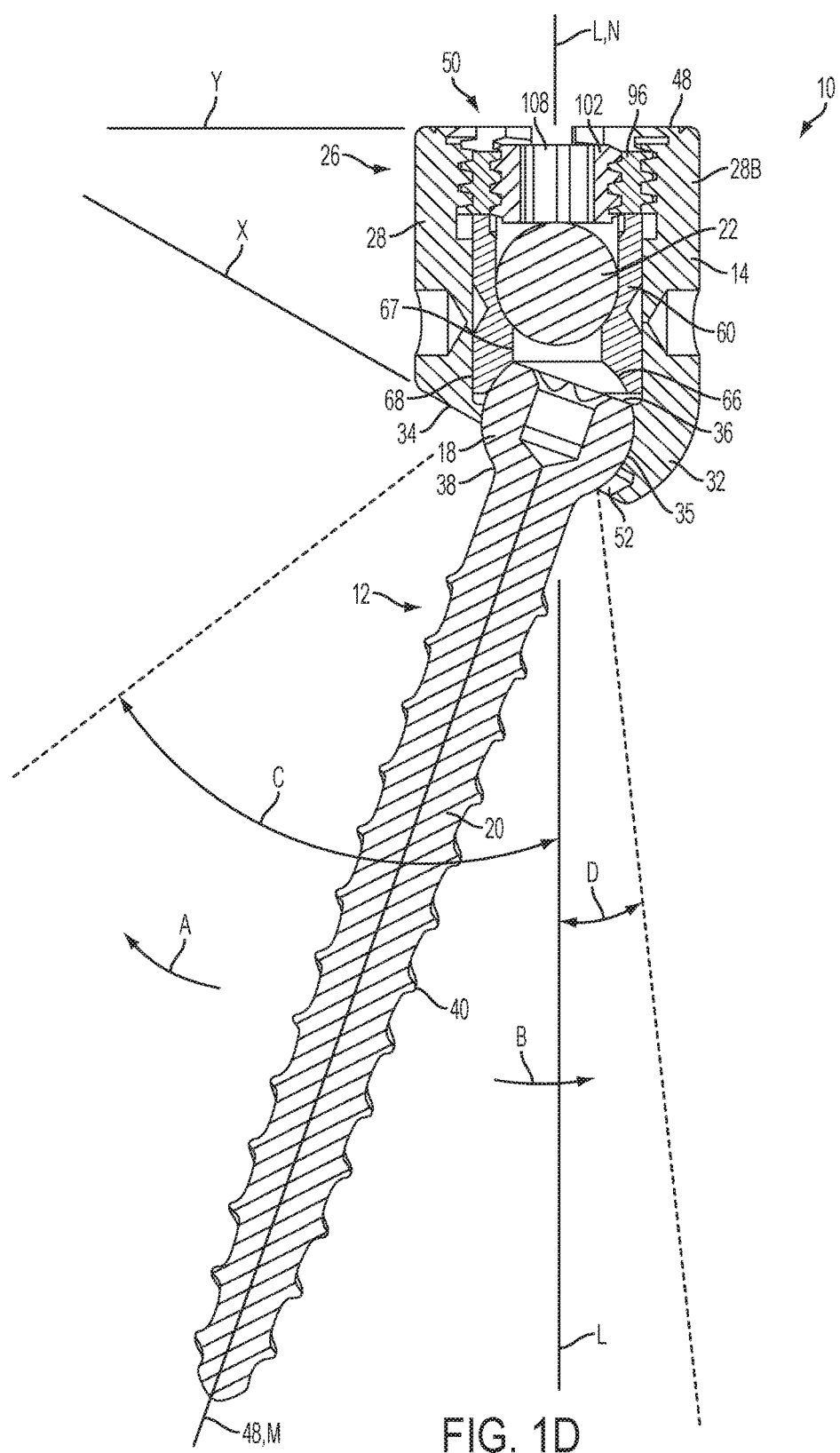
FIG. 1D is a cross-sectional view of the bone anchor assembly of FIG. 1A.

As best seen in FIG. 1B, the compression member 60 is configured to slide freely along the longitudinal axis L within the recess 30 of the receiver member 14. To secure the compression member 60 within the receiver member 14, the compression member 60 can be configured to mate with the receiver member, for example by mechanically deforming a portion of the compression member 60 against the receiver member 14. In the illustrated embodiment, opposing bores formed in the arms 62A, 62B of the compression member 60 are aligned with bores formed in the arms 62A, 62B of the receiver member 14, such that opposing pins can be inserted through the passageways defined by the bores to compress or "swage" the compression member 60 against the receiver member 14. The swaging process can prevent subsequent removal of the compression member 60 from the receiver member 14.

The proximal end 26 of the receiver member 14 can be configured to receive a closure mechanism 16 positionable between and engaging the arms 28A, 28B of the receiver member 14. The closure mechanism 16 can be configured to capture a spinal fixation element, e.g., a spinal rod 22, within the receiver member 14, to fix the spinal rod 22 relative to the receiver member 14, and to fix the bone anchor 12 relative to the receiver member 14. The closure mechanism 16 can be a single set screw having an outer thread for engaging an inner thread 42 provided on the arms 28A, 28B of the receiver member 14. In the illustrated embodiment, however, the closure mechanism 16 comprises an outer set screw 70 positionable between and engaging the arms 28A, 28B of the receiver member 14 and an inner set screw 72 positionable within the outer set screw 70. The outer set screw 70 is operable to act on the compression member 60 to fix the bone anchor 12 relative to the receiver member 14. The inner set screw 72 is operable to act on the spinal rod 22 to fix the spinal rod 22 relative to the receiver member 14. In this manner, the closure mechanism 16 permits the bone anchor 12 to be fixed relative to the receiver member 14 independently of the spinal rod 22 being fixed to the receiver member 14. In particular, the outer set screw 70 can engage the proximal end surfaces of the arms 62A, 62B of the compression member 60 to force the distal-facing surface 66 of the compression member 60 into contact with the proximal head 18 of bone anchor 12, which in turn forces the distal surface 38 of the proximal head 18 into fixed engagement with the distal inner surface of the receiver member 14. The inner set screw 72 can engage the spinal rod 22 to force the spinal rod 22 into fixed engagement with the rod seat 64 of the compression member 60.

The outer set screw 70 includes a first outer thread 74 for engaging a complementary inner thread 42 on the arms 28A, 28B of the receiver member 14. The outer set screw 74 includes a central passage 96 from a top surface 98 of the outer set screw 74 to a bottom surface 100 of the outer set screw 74 for receiving the inner set screw 72. The central passage 96 can includes an inner thread 102 for engaging a complementary outer thread 104 on the inner set screw 72. The thread form for the inner thread 102 and the outer thread 104, including the number of threads, the pitch, major and minor diameter, and thread shape, can be selected to facilitate connection between the components and transfer of the desired axial tightening force. The top surface 98 of the outer set screw 74 can have one or more drive features to facilitate rotation and advancement of the outer set screw 74 relative to the receiver member 14. The illustrated outer set screw 74 includes drive features in the form of a plurality of cut-outs 106 spaced-apart about the perimeter of the top surface 98. The inner set screw 104 can include drive features for receiving an instrument to rotate and advance the inner set screw 72 relative to the outer set screw 74. The illustrated inner set screw 104 includes drive features in the form of a central passage 108 having a plurality of spaced apart, longitudinally oriented cut-outs for engaging complementary features on an instrument.

The bone anchor assembly 10 can be used with a spinal fixation element such as rigid spinal rod 22. The various components of the bone anchor assemblies disclosed herein, as well as the spinal rod 22, can be constructed from various materials, including titanium, titanium alloys, stainless steel, cobalt chrome, PEEK, or other materials suitable for rigid fixation. In other embodiments, the spinal fixation element can be a dynamic stabilization member that allows controlled mobility between the instrumented vertebrae.

In use, bone can be prepared to receive the bone anchor assembly 10, generally by drilling a hole in the bone which is sized appropriately to receive the bone anchor 12. If not already completed, the bone anchor assembly 10 can be assembled, which can include assembling the bone anchor 12 and the receiver member 14, so that the distal shaft 20 extends through the opening in the distal end 32 of the receiver member 14 and the proximal head 18 of the bone anchor 12 is received in the distal end 32 of the receiver member 14. A driver tool can be fitted with the bone anchor 12 to drive the bone anchor 12 into the prepared hole in the bone. The compression member 60 can be positioned within the receiver member 14 such that the arms 62A, 62B of the compression member are aligned with the arms 28A, 28B of the receiver member 14 and the lower surface of the compression member 14 is in contact with the proximal head 18 of the bone anchor 12. A spinal fixation element, e.g., the spinal rod 22, can be located in the recess 30 of the receiver member 14. The closure mechanism 16 can be engaged with the inner thread 42 provided on the arms 28A, 28B of the receiver member 14. A torsional force can be applied to the outer set screw 70 to move it within the recess 30 using a tool which can engage the plurality of cut-outs 106 in the upper facing surface of the outer set screw 70, so as to force the compression member 60 onto the proximal head 18 of the bone anchor 12. Torsional forces can then be applied to the inner set screw 72 to move it relative to the outer set screw 70 so that it contacts the spinal rod 22 and can, for example, fix the spinal rod 22 relative to the receiver member 14 and the bone anchor 12.

Figure 8:
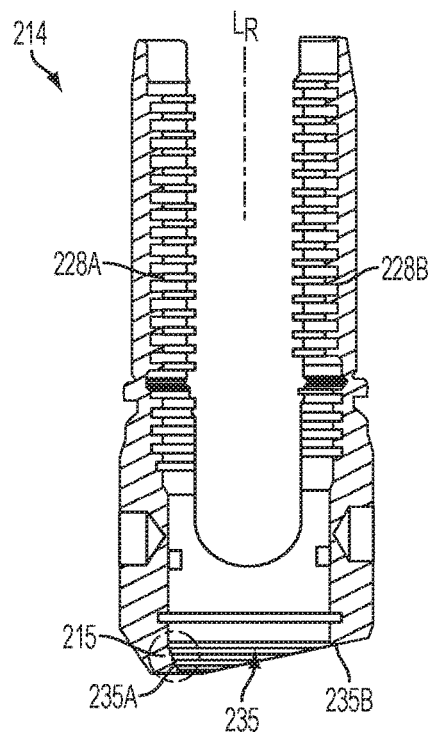
FIG. 8 is a cross-sectional view of a receiver member for use with a bone anchor assembly.
Figure 9:
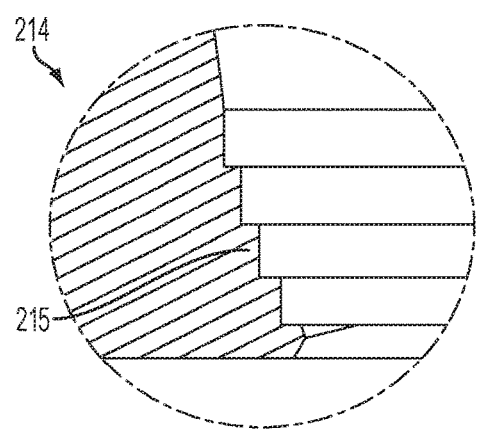
FIG. 9 is a partial cross-sectional view of the receiver member of FIG. 8.
Figure 10:
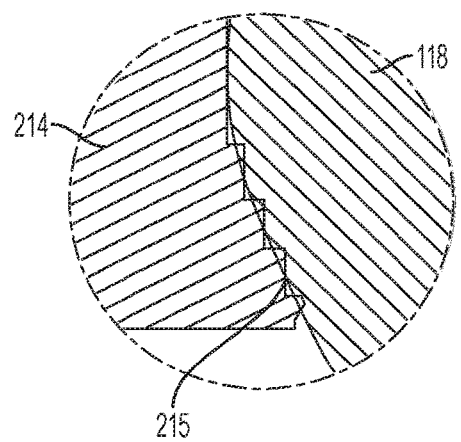
FIG. 10 is a partial cross-sectional view of the receiver member of FIG. 8 having a bone anchor seated therein.

One or more embodiments of inventive bone anchor assemblies are described below. Except as indicated below, the structure, operation, and use of these embodiments is similar or identical to that of the bone anchor assembly 10 described above. Accordingly, a detailed description of said structure, operation, and use is omitted here for the sake of brevity. FIGS. 2-7 show various embodiments of compression members similar to the compression member 60 shown in FIG. 1B and having gripping features on a distal end thereof for gripping a head of a bone anchor with greater friction as compared with a distal end formed as a negative of the head portion of the bone anchor. The compression members shown in FIGS. 2-7 can be used with the bone anchor assembly shown in FIGS. 1A-1D, or with various other bone anchor assemblies known in the art. FIGS. 8-10 show various embodiments of receiver member similar to the receiver member 14 shown in FIG. 1B and having gripping features formed within a distal recess therein for gripping the underside of a head of a bone anchor with greater friction as compared with a recess in a receiver formed as a negative of the head portion of the bone anchor. The receiver members shown in FIGS. 8-10 can be used with the bone anchor assembly shown in FIGS. 1A-1D, or with various other bone anchor assemblies known in the art.

Figure 2:
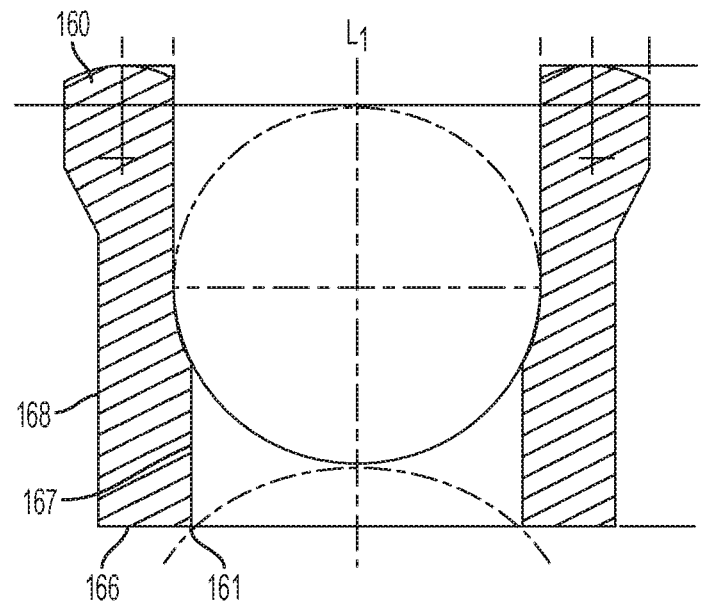
FIG. 2 is a cross-sectional view of one embodiment of a compression member for use with a bone anchor assembly.

FIG. 2 illustrates an exemplary embodiment of a compression member for use with a bone anchor assembly of the type described above. The illustrated compression member 160 has a distal end that is configured to grip a proximal head of a bone anchor to secure the head at a desired angle with respect to a receiver member (not shown) when the compression member is locked within the receiver member, e.g., when a closure mechanism is applied to the receiver member to lock the bone anchor in a fixed position relative to the receiver member. Although the distal end of the compression member 160 can be configured to grip the head of a bone anchor in a variety of ways, in the illustrated embodiment, the compression member 160 includes a planar distal-facing surface 166 that extends between an inner cylindrical surface 167 and an outer cylindrical surface 168. The distal-facing surface 166 can extend in a plane perpendicular to the longitudinal axis $L_1$ of the compression member 160, and the surface can have a generally circular shape with an inner circular corner or edge 161. When the compression member 160 is secured locked within a receiver member, the edge 161 can create a ring-shaped line contact with the head of the bone anchor to substantially prevent movement of the head and to ensure that the bone anchor remains at a fixed angle with respect to the receiver member. Such line contact can be particularly advantageous with favored-angle bone anchors in which the bone anchor is at an extreme angle relative to the receiver member. As explained above with respect to FIGS. 1A-1D, the compression member 160 can be locked within the receiver member by applying a closure mechanism, e.g., inner and/or outer set screws, to the receiver member. The closure mechanism can apply a distally directed force to a spinal fixation element, e.g., a spinal rod, seated within the receiver member, and the spinal rod in turn can apply a distally directed force to the compression member 160 to cause the compression member 160 to press down on and engage the head of the bone anchor. In other embodiments, the closure mechanism can be configured to provide a force directly to the compression member 160 to lock the head of the bone anchor in a fixed position relative to the receiver member without locking the spinal fixation rod within the receiver member. For example, the closure mechanism can include inner and outer set screws, with the inner set screw locking the rod and the outer set screw locking the compression member and thus the bone anchor. A person skilled in the art will appreciate that a variety of locking techniques can be utilized.

The configuration of the edge 161 can vary, and in one embodiment the edge 161 can have a radius of curvature corresponding to a radius of curvature of the head of a bone anchor to be used therewith. In some embodiments, a largest diameter of the edge 161 can be smaller than a diameter of the head where the edge 161 grips the head to create an interference fit between the compression member 160 and the head. In the illustrated embodiment, the edge 161, and thus the ring-shaped line contact, extends in a plane that is substantially perpendicular to a longitudinal axis $L_1$ of the compression member 160, but it will be appreciated by a person skilled in the art that the line contact can be formed in a plane that is oriented at any angle to the longitudinal axis $L_1$ of the compression member 160.

FIGS. 3-7 illustrate additional embodiments of compression members with distal-facing surfaces having various shapes and various gripping features thereon configured to grip a head of a bone anchor when the compression member is in a locked configuration. The compression members of FIGS. 3-7 can generally be configured and used similar to the compression member 160 of FIG. 2. Additionally, like-named elements and like-illustrated elements of the compression member 160 and of the other compression members discussed herein can be configured and used similar to one another.

Figure 3:
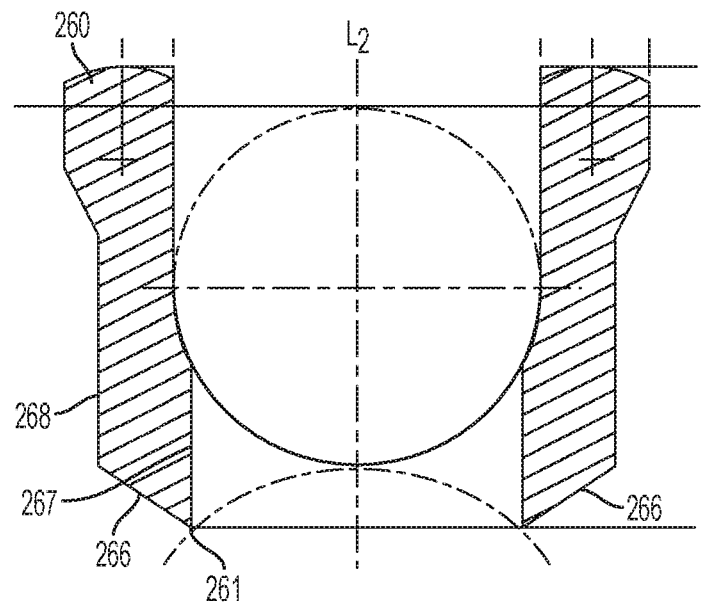
FIG. 3 is a cross-sectional view of another embodiment of a compression member for use with a bone anchor assembly.

In the embodiment of FIG. 3, the compression member 260 has a sloped distal-facing surface 266 that extends between an inner cylindrical surface 267 and an outer cylindrical surface 268, the inner and outer surfaces 267, 268 defining the inner and outer sidewalls of the compression member 260. The inner surface 267 can extend distally beyond the outer surface 268, such that the distal-facing surface 266 can be oriented at an angle to a longitudinal axis $L_2$ of the compression member 260 and such that the distal-facing surface 266 forms a cone. A distal-most tip of the cone terminates in a sharp edge 261. Similar to the edge 161 of compression member 160 of FIG. 2, the edge 261 in FIG. 3 can form a ring-shaped line contact with the head of the bone anchor to facilitate gripping of the head. The sloped orientation of the distal-facing surface 266 can increase a sharpness of the edge 261 such that the edge 261 is configured to dig into the head and further reduce a risk of slippage of the head of a bone anchor with respect to the receiver member.

Figure 4:
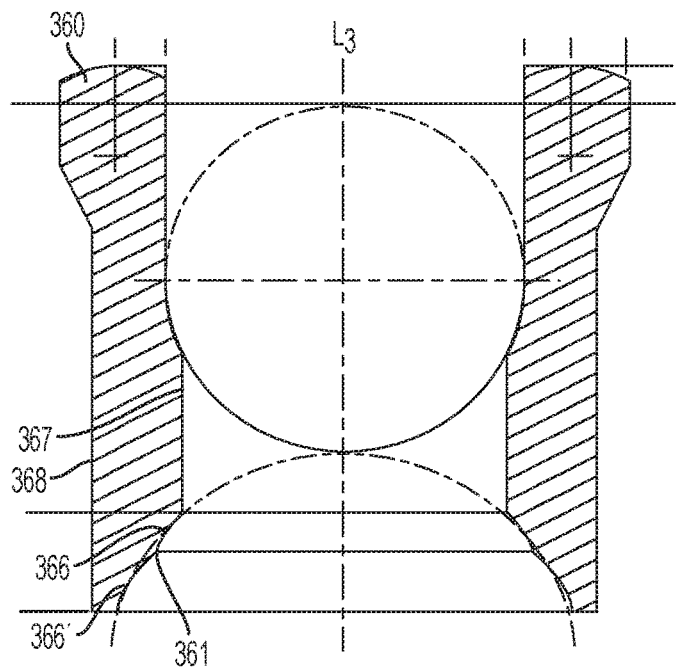
FIG. 4 is a cross-sectional view of another embodiment of a compression member for use with a bone anchor assembly.

Referring now to FIG. 4, in another embodiment a compression member 360 can have a first spherically shaped distal-facing surface 366 and second spherically shaped distal-facing surface 366' extending distally from the first distal-facing surface 366. The first distal facing surface 366 can have a radius of curvature that is different, e.g., less, than a radius of curvature of the second distal-facing surface 366', such that a ring-shaped crest 361 is formed at the intersection of the first distal-facing surface 366 and the second distal-facing surface 366' for gripping the head of a bone anchor. A largest diameter of the crest 361 can be smaller than a diameter of the head of the bone anchor where the crest 361 grips the head, thus creating an interference fit between the compression member 360 and the head. The dimensions of the crest 361 as shown in FIG. 4 are exaggerated for the sake of illustration. While the position of the crest 361 can vary, in the illustrated embodiment the crest is shown at a general mid-portion of the distal-facing surface such that a height of the first distal-facing surface 366 is substantially the same as a height of the second distal-facing surface 366'. This configuration can allow the edge 361 to engage the head of the bone anchor at a desirable location. A person skilled in the art will appreciate, however, that the location of the edge 361 can vary as may be desired based on the size of the head of the bone anchor. Moreover, as with the embodiment of FIG. 2, the edge 361 can extend at any angle relative to the longitudinal axis $L_3$, including perpendicular or at some other angle.

Figure 5:
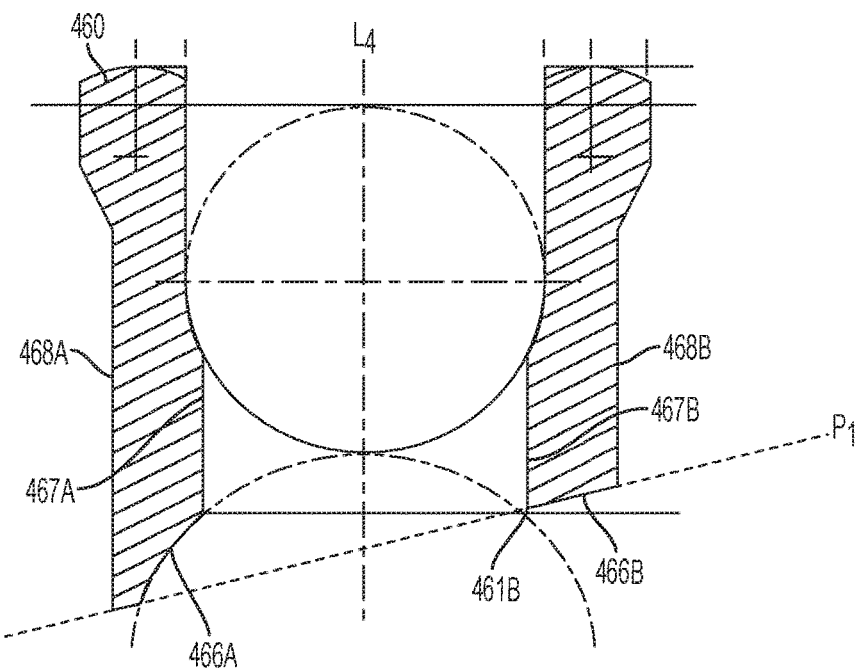
FIG. 5 is a cross-sectional view of another embodiment of a compression member for use with a bone anchor assembly.

FIG. 5 illustrates another embodiment of a compression member 460 having an angled distal-facing surface that extends in a plane $P_1$ that is transverse and non-perpendicular to the longitudinal axis $L_4$ of the compression member 460. As a result, the compression member 460 can have a first hemicylindrical portion 468A that extends distally beyond a distal-most end of a second hemicylindrical portion 468B such that a first distal-facing surface 466A can be distal and offset along a longitudinal axis $L_4$ of the compression member 460 from a second distal-facing surface 466B. The angled distal-facing surface can also cause the first distal-facing surface 466A to have a shape that differs a shape of the second distal-facing surface 466B. In particular, the compression member 460 can have a generally spherical recess formed in the distal end thereof, and the spherical recess can have a center point (not shown) that is positioned along the longitudinal axis $L_4$ of the compression member 460. The plane $P_1$ can intersect the perimeter of the sphere at a location (shown as edge 461B) that causes the second distal-facing surface 466B to be co-planar with plane $P_1$. The second distal-facing surface 466B will thus define an edge 461B for creating a semicircular line contact with the head of a bone anchor, whereas the spherical shape of the first distal-facing surface 466A will form a negative of a portion of the head against which the first distal-facing surface 466A abuts. The first distal-facing surface 466A will thus support the head on one end of the head while the edge 461B on the second distal-facing surface 466B can cut into the head at an opposed end of the head. The compression member 460 can thus exert a compressive force on the head that acts at an angle to the longitudinal axis $L_4$ of the compression member 460 and that can balance an opposing resistive force of the bone anchor against the compression member 460 when the bone anchor is oriented at an angle to the longitudinal axis $L_4$. As further shown in FIG. 5, the first distal-facing surface 466A can have a radius of curvature corresponding to a radius of curvature of a head of a bone anchor where the first distal-facing surface 466A grips the head, although the radius of curvature of the first distal-facing surface 466A can be smaller than the radius of curvature of the head to create an interference fit with the head. In one embodiment, a largest diameter of an inner cylindrical surface 467 of the compression member 460 can be smaller than a diameter of the head where the compression member 460 grips the head.

Figure 6:
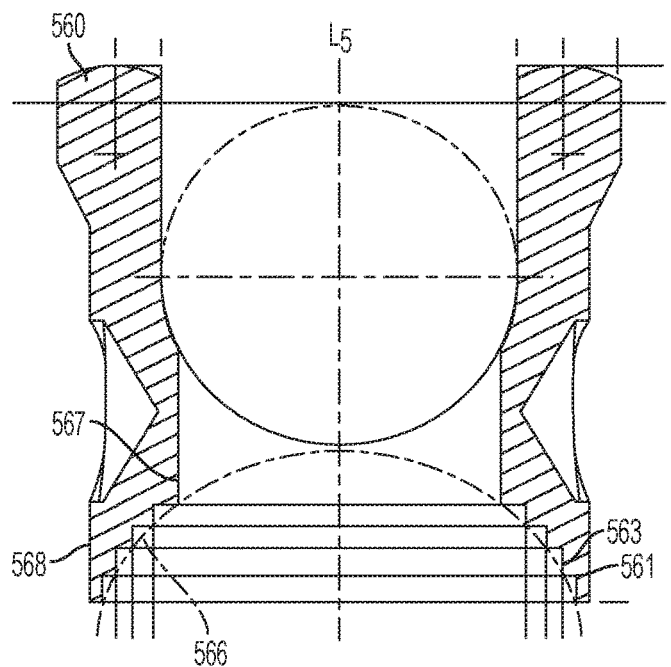
FIG. 6 is a cross-sectional view of another embodiment of a compression member for use with a bone anchor assembly.

In another embodiment, a distal end of a compression member can have multiple gripping features thereon to facilitate gripping a head of a bone anchor. By way of non-limiting example, FIG. 6 illustrates a compression member 560 having a plurality of teeth 563 formed on a distal-facing surface 566. As with previous embodiments, the distal-facing surface 566 can extend between an inner cylindrical surface 567 and an outer cylindrical surface 568, with the inner and outer cylindrical surfaces 567, 568 defining inner and outer sidewalls of the compression member. Similar to the edge 261 described above and illustrated in FIG. 3, sharp crests 561 of the teeth 563 can grip the head of a bone anchor along ring-shaped line contacts to reduce a risk of slippage. The teeth 563 can impart the additional advantage of providing multiple line contacts with the head to provide a stronger grip on the head. Each of the crests 561 can have a radius of curvature, either the same or different from one another, corresponding to the radius of curvature of the head. A largest diameter of at least one of the crests 561 can be slightly smaller than a diameter of the head where the at least one of the crests 561 grips the head to create an interference fit between the compression member 560 and the head.

The teeth 563 can be of any size, shape, and number. In the illustrated embodiment of FIG. 6, the teeth 563 include two planar, substantially perpendicular side walls that meet at the sharp crests 561, although the side walls of the teeth can be oriented at various angles with respect to one another to form sharper or duller crests 561. The teeth 563 can extend along any distance around a circumference of the distal-facing surface 566, although in the illustrated embodiment the teeth 563 extend along the entire circumference of the distal-facing surface 566. Each of the teeth 563 extend in a plane that is substantially perpendicular to a longitudinal axis $L_5$ of the compression member 560, but the teeth 563 can be oriented in any plane, either the same or different from one another. Moreover, the teeth 563 can be disposed along the distal-facing surface 566 at any distance from one another, although the teeth 563 of the illustrated embodiment are disposed at regular intervals along the longitudinal axis $L_5$ of the compression member 560. In one aspect, the teeth can be composed of one or more flexible materials, such that the teeth 563 are configured to deform upon contact with the head of a bone anchor. In this embodiment, the teeth 563 can form ring-shaped band contacts with the head, the band contacts having a width measured along the longitudinal axis $L_5$ of the compression member 560 that corresponds to an amount of deformation of the teeth 563.

Figure 7:
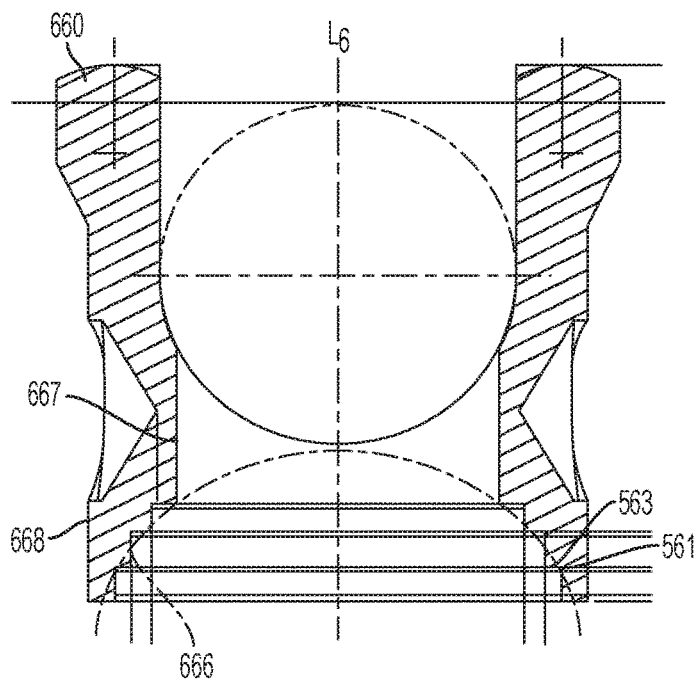
FIG. 7 is a cross-sectional view of another embodiment of a compression member for use with a bone anchor assembly.

FIG. 7 illustrates another embodiment of a compression member 660 having teeth 663 for gripping the head, in which the teeth 663 can each have spherical surfaces 661 such that the teeth 663 can form a plurality of ring-shaped band contacts with the head of a bone anchor. The teeth 663 can be configured similarly to the teeth 553 of the compression member 560 of FIG. 6, however the spherical shape of the spherical surfaces 661 of the teeth 663 can simplify the manufacturing process and can reduce a risk of deformation of the head by the teeth 663. To further reduce a risk of deformation of the head by the teeth 663, the teeth 663 can be comprised of one or more flexible materials, such that the teeth 663 are configured to deform into contact with the head along the ring-shaped band contacts.

A person skilled in the art will appreciate that all of the aforementioned features for increasing engagement between a compression member and a bone anchor can be provided on a receiver member so as to similarly increase engagement between a receiver member and a bone anchor. The gripping features of the receiver member can be used either in place of or in addition to gripping features formed on a compression member, and can be of any size, shape, and number. FIG. 8 illustrates one example of a receiver member 214 having a distal end 232 with a plurality of teeth 215 configured to grip the head of a bone anchor. The teeth 215, shown in more detail in FIG. 9, can be formed on a distal inner surface 235 of the receiver member 214 that is configured to polyaxially seat the head of a bone anchor, and can be of any size, shape, and number, similar to those discussed above regarding compression members 560 and 660 of FIGS. 6 and 7. The teeth 215 can extend around any portion of the circumference of the distal inner surface 235 and can be positioned at various locations along a length measured along a longitudinal axis LR of the receiver member 214. As shown in FIG. 10, the teeth 215 can cut into the head to substantially prevent movement of the head when the receiver member 214 is locked to the bone anchor. In the illustrated embodiment, the receiver member 214 is a favored-angle receiver having teeth 215 formed only on a first portion 235A of the distal inner surface 235, i.e., on a distal-most end that extends distally beyond a distal-most end of an opposed second portion 235B of the distal inner surface 235. The distal-most end of the second portion 235B can be in the form of an edge that is opposed from the teeth 215 and can thus provide for opposed clamping of the head 18 similar to that described above with respect to the compression member 460 of FIG. 5.

In use, a bone anchor assembly can be assembled, either during manufacturing, prior to use, or intraoperatively, by passing an elongate shank of a bone anchor in a proximal-to-distal direction through an aperture formed in a distal end of a receiver member. In other embodiments, bottom-loading bone anchors can be utilized. A proximal head portion of the bone anchor can be polyaxially seated within the polyaxial recess in the receiver member. A compression member can be inserted between the opposed arms of the receiver member, proximal to the proximal head of the bone anchor. An angle of the bone anchor with respect to the receiver member can be adjusted to a desired angle. In an exemplary embodiment, the compression member is configured to apply a frictional force to the bone anchor to maintain the bone anchor in a desired angular orientation prior to lock, while still allowing a force to be applied to the bone anchor to move the bone anchor relative to the receiver member.

Figure 11:
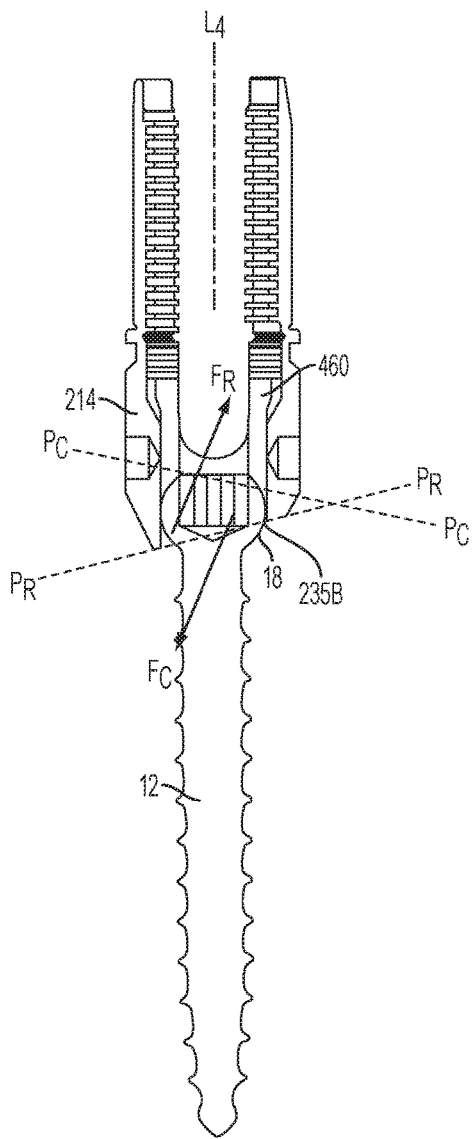
FIG. 11 is a cross-sectional view of a bone anchor assembly showing the compression member of FIG. 5 oriented in a first orientation relative to the receiver member of FIG. 8.
Figure 12:
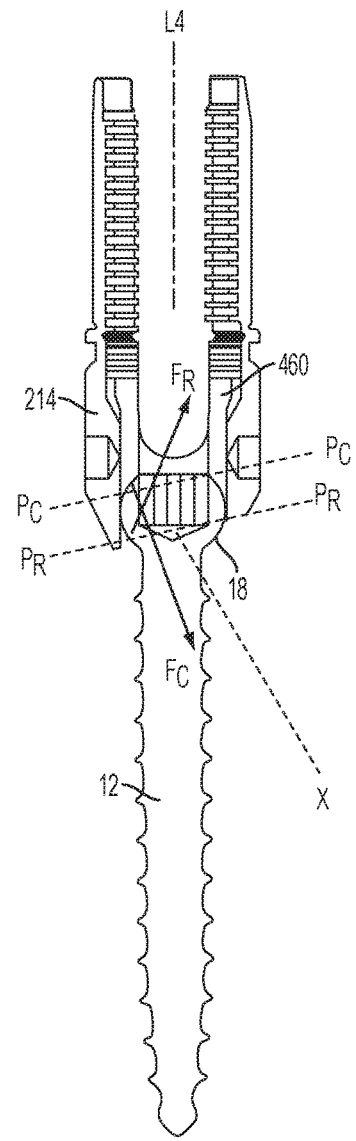
FIG. 12 is a cross-sectional view of another a bone anchor assembly showing the compression member of FIG. 5 oriented in a second orientation relative to the receiver member of FIG. 8.

During an implantation procedure, the bone can be prepared to receive the bone anchor, e.g., by drilling an appropriately sized hole. A driver tool can be fitted with the bone anchor to drive the bone anchor into the prepared hole in the bone. A spinal fixation element, e.g., a rod, can be located in between the arms of the receiver member, and a closure mechanism can be applied to the receiver member, proximally of the rod, to urge the spinal rod and the compression member distally such that a distal-facing surface of the compression member comes into contact with the head of the bone anchor. Gripping features of the compression member can grip the head of the bone anchor to grip the head portion of the bone anchor with greater friction as compared with a distal end formed as a negative of the head portion of the bone anchor on the head of the bone anchor. In particular, the compression member can make at least one of line contact and band contact with the head portion of the bone anchor. As a result, the bone anchor is locked at the desired angle with respect to the receiver member. Similarly, or alternatively, gripping features on the receiver member can have the same effect to lock the receiver member in a fixed position relative to the bone anchor. Such gripping features on the compression member and/or the receiver member can provide increased contact and further prevent the risk of slippage as compared to compression members and receivers lacking such features.

Where a bone anchor assembly includes both a favored-angle receiver member, such as receiver 214 shown in FIG. 8, and a favored-angle compression member, such as compression member 460 shown in FIG. 5, the angled distal-surfaces can be oriented relative to one another so as to direct the compressive forces in a desired direction. For example, as shown in FIG. 11, the distal-facing surface of compression member 460 extends in a plane $P_C$ that is transverse and non-perpendicular to a plane $P_R$ of the distal-facing surface of the receiver member 214. As a result, a compressive force $F_C$ exerted by the compression member 460 can act on one side of the head 18 of the bone anchor in a direction that is opposite to a compressive force $F_R$ exerted by the receiver member 214 on the opposite side of the head 18. Both compressive forces $F_C$, $F_R$ can act at an angle to the longitudinal axis $L_4$ of the compression member 460 and can counterbalance one another to stabilize the bone anchor 12. Conversely, in FIG. 12, the plane $P_C$ of the distal-facing surface of the compression member 460 is oriented substantially parallel to the plane $P_R$ of the distal-facing surface of the receiver member 214. In this configuration, the compressive forces $F_C$, $F_R$ exerted by the compression member 460 and the receiver member 214 can act on a same side of the head 18 but in opposite proximal-distal directions. This alignment of compressive forces $F_C$, $F_R$ can similarly help to stabilize the head 18, particularly where the bone anchor 12 is oriented at an angle to the longitudinal axis $L_4$ of the compression member 460 in a direction X as shown in FIG. 12. A person skilled in the art will appreciate that the planes $P_C$, $P_R$ of the distal-facing surfaces of the compression member 460 and receiver member 214 can be oriented in a desired configuration during manufacturing, e.g., via a swaging process described above, or before or during surgery.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A bone anchor assembly, comprising:
   a bone anchor having a proximal head portion and a distal shank portion;
   a receiver member having a polyaxial seat formed therein for polyaxially seating the head portion of the bone anchor; and
   a compression member configured to be disposed within the receiver member, the compression member having an inner sidewall surface and a concentric outer sidewall surface connected by a spherically shaped distal-facing surface that extends from the inner sidewall surface to a distal-most end surface of the compression member;
   wherein a proximal portion of the compression member includes a pair of spaced apart arms defining a U-shaped seat for receiving a spinal fixation element;
   wherein the spherically shaped distal-facing surface includes a tooth formed thereon and disposed between a first intersection of the inner sidewall surface and the distal-facing surface and a second intersection of the distal-most end surface and the distal-facing surface;
   wherein the tooth extends around an entire circumference of the distal-facing surface such that a crest of the tooth is configured to make a ring-shaped line contact with the head portion of the bone anchor; and
   wherein a distal-most portion of the outer sidewall surface defines a continuous cylinder having a single diameter.

2. The bone anchor assembly of claim 1, wherein the tooth extends around the entire circumference of the distal-facing surface of the compression member in a plane that is perpendicular to a longitudinal axis of the compression member.

3. The bone anchor assembly of claim 1, wherein the tooth extends around the entire circumference of the distal-facing surface of the compression member in a plane that is at a non-perpendicular angle to a longitudinal axis of the compression member.

4. The bone anchor assembly of claim 1, wherein the outer sidewall surface and the inner sidewall surface are cylindrically shaped.

5. The bone anchor assembly of claim 1, wherein the distal-facing surface is shaped as a negative of the proximal head portion of the bone anchor.

6. The bone anchor assembly of claim 1, wherein a largest diameter of the crest of the tooth is smaller than a diameter of the proximal head portion of the bone anchor.

7. The bone anchor assembly of claim 1, wherein the tooth includes two planar, substantially perpendicular sidewalls that meet at the crest.

8. The bone anchor assembly of claim 1, wherein the tooth is the only feature formed on the distal-facing surface.

9. The bone anchor assembly of claim 1, further comprising a set screw having an outer thread configured to engage an inner thread formed on the receiver member such that the set screw can contact a proximal portion of the compression member as it is threaded into the receiver member.

10. The bone anchor assembly of claim 9, wherein the set screw includes a central passage from a top surface thereof to a bottom surface thereof, the central passage including an inner thread configured to engage an outer thread of a second set screw.

11. A bone anchor assembly, comprising:
a bone anchor having a proximal head portion and a distal shank portion;
a receiver member having a polyaxial seat formed therein for polyaxially seating the head portion of the bone anchor; and
a compression member configured to be disposed within the receiver member, the compression member having an inner sidewall surface and a concentric outer sidewall surface connected by a distal-facing surface that is shaped as a negative of the proximal head portion of the bone anchor and extends from the inner sidewall surface to a distal-most end surface of the compression member;
wherein a proximal portion of the compression member includes a pair of spaced apart arms defining a U-shaped seat for receiving a spinal fixation element;
wherein the distal-facing surface includes a gripping feature formed thereon and disposed between a first intersection of the inner sidewall surface and the distal-facing surface and a second intersection of the distal-most end surface and the distal-facing surface;
wherein the gripping feature is configured to grip the proximal head portion of the bone anchor with greater friction as compared to the distal-facing surface formed as a negative of the proximal head portion of the bone anchor; and
wherein a distal-most portion of the outer sidewall surface has a first maximum diameter and a proximal-most portion of the outer sidewall surface has a second maximum diameter that is larger than the first maximum diameter.

12. The bone anchor assembly of claim 11, wherein the gripping feature extends around an entire circumference of the distal-facing surface of the compression member.

13. The bone anchor assembly of claim 12, wherein the gripping feature extends around the entire circumference of the distal-facing surface of the compression member in a plane that is perpendicular to a longitudinal axis of the compression member.

14. The bone anchor assembly of claim 12, wherein the gripping feature extends around the entire circumference of the distal-facing surface of the compression member in a plane that is at a non-perpendicular angle to a longitudinal axis of the compression member.

15. The bone anchor assembly of claim 11, wherein the outer sidewall surface and the inner sidewall surface are cylindrically shaped.

16. The bone anchor assembly of claim 11, wherein the distal-facing surface is spherically shaped.

17. The bone anchor assembly of claim 11, wherein the gripping feature is the only feature formed on the distal-facing surface.

18. A bone anchor assembly, comprising:
a bone anchor having a proximal spherically-shaped head portion and a distal shank portion;
a receiver member having a polyaxial seat formed therein for polyaxially seating the head portion of the bone anchor; and
a compression member configured to be disposed within the receiver member, the compression member having an inner sidewall surface and a concentric outer sidewall surface connected by a distal-facing spherically-shaped surface that extends from the inner sidewall surface to a distal-most end surface of the compression member;
wherein a proximal portion of the compression member includes a pair of spaced apart arms defining a U-shaped seat for receiving a spinal fixation element;
wherein the distal-facing spherically-shaped surface includes a single tooth formed thereon and extending from the distal-facing spherically-shaped surface at a location spaced apart from a first intersection between the inner sidewall surface and the distal-facing surface and a second intersection between the distal-most end surface and the distal-facing surface;
wherein the single tooth extends around an entire circumference of the distal-facing surface such that a crest of the tooth is configured to make a ring-shaped line contact with the head portion of the bone anchor; and
wherein the pair of spaced apart arms of the compression member each includes a bore formed therein that aligns with a bore formed in a proximally-extending arm of the receiver member when the compression member is disposed within the receiver member.

* * * * *